US009155168B2

(12) United States Patent
Araujo et al.

(10) Patent No.: US 9,155,168 B2
(45) Date of Patent: Oct. 6, 2015

(54) WEARABLE LIGHTING DEVICE

(75) Inventors: Luis Araujo, Las Vegas, NV (US);
Kevin Skehan, Las Vegas, NV (US);
Douglas J. Port, Huntington Beach, CA (US); Ammar Burayez, Silverado, CA (US)

(73) Assignee: SureFire, LLC, Fountain Valley, CA (US)

(*) Notice: Subject to any disclaimer, the term of this patent is extended or adjusted under 35 U.S.C. 154(b) by 0 days.

(21) Appl. No.: 12/960,376

(22) Filed: Dec. 3, 2010

(65) Prior Publication Data

US 2012/0140451 A1    Jun. 7, 2012

(51) Int. Cl.
| *F21V 21/08* | (2006.01) |
| *H05B 37/02* | (2006.01) |
| *F21V 23/04* | (2006.01) |
| *A61B 5/00* | (2006.01) |
| *F21L 4/00* | (2006.01) |
| *G01S 19/14* | (2010.01) |
| *G01S 19/35* | (2010.01) |
| *G04G 17/08* | (2006.01) |
| *G04G 21/00* | (2010.01) |
| *A61B 5/11* | (2006.01) |
| *F41G 1/35* | (2006.01) |

(52) U.S. Cl.
CPC .............. *H05B 37/0227* (2013.01); *A61B 5/11* (2013.01); *A61B 5/681* (2013.01); *F21L 4/005* (2013.01); *F21V 23/0492* (2013.01); *F41G 1/35* (2013.01); *G01S 19/14* (2013.01); *G01S 19/35* (2013.01); *G04G 17/08* (2013.01); *G04G 21/00* (2013.01); *A61B 5/6824* (2013.01)

(58) Field of Classification Search
CPC ......... F21L 11/00; F21V 33/0004; F41G 1/35
USPC ................................... 362/103, 104
See application file for complete search history.

(56) References Cited

U.S. PATENT DOCUMENTS

| 1,769,241 A | * | 7/1930 | Stephani | ........................ 362/103 |
| 2,399,511 A | * | 4/1946 | Sabiers | ........................ 248/688 |
| 2,805,326 A | | 11/1955 | Schwartz | |
| 3,112,889 A | * | 12/1963 | Marmo et al. | ................. 362/103 |

(Continued)

FOREIGN PATENT DOCUMENTS

| GB | 2255402 | 11/1992 |
| GB | 2417186 | 2/2006 |
| WO | WO-97/31219 | 8/1997 |

OTHER PUBLICATIONS

U.S. Appl. No. 29/380,426, Araujo et al.

(Continued)

*Primary Examiner* — Robert May
*Assistant Examiner* — Bryon T Gyllstrom
(74) *Attorney, Agent, or Firm* — Haynes and Boone, LLP

(57) ABSTRACT

A user wearable device may be implemented with a light source to provide illumination to an area of interest. In one example, the light source may be selectively operated by switches, physical displacement (e.g., movement) of the device, or other approaches. In another example, the device may be implemented as a wristwatch to display time, date, or related information to a user. In another example, the device may be implemented with appropriate processing or communication components to perform other tasks. In other embodiments, various methods of using, operating, or manufacturing such devices are provided.

32 Claims, 13 Drawing Sheets

(56) References Cited

U.S. PATENT DOCUMENTS

| | | | |
|---|---|---|---|
| 4,319,309 A | 3/1982 | Benoit | |
| 4,425,600 A | 1/1984 | Barnhart | |
| 4,788,631 A * | 11/1988 | Fuller | 362/103 |
| D324,579 S | 3/1992 | Crabtree, Jr. | |
| 5,191,197 A | 3/1993 | Metlitsky et al. | |
| 5,193,896 A | 3/1993 | Oberlander | |
| D353,012 S | 11/1994 | Mihavetz | |
| D361,143 S | 8/1995 | Helvey | |
| D362,736 S | 9/1995 | Leather | |
| 5,580,154 A * | 12/1996 | Coulter et al. | 362/103 |
| 5,775,792 A * | 7/1998 | Wiese | 362/328 |
| 5,904,280 A | 5/1999 | Chan | |
| 6,213,619 B1 * | 4/2001 | Yu | 362/103 |
| 6,550,930 B1 | 4/2003 | Portouche | |
| D485,382 S | 1/2004 | Palm | |
| D500,377 S | 12/2004 | Yamamoto et al. | |
| 7,023,763 B2 | 4/2006 | Galli | |
| D524,974 S | 7/2006 | Zernov | |
| D525,734 S | 7/2006 | Shiao | |
| D526,079 S | 8/2006 | Heun | |
| D531,335 S | 10/2006 | Garrity | |
| D556,927 S | 12/2007 | Shiu | |
| 7,303,306 B2 * | 12/2007 | Ross et al. | 362/191 |
| D560,008 S | 1/2008 | Poon | |
| D567,975 S | 4/2008 | Wright et al. | |
| 7,399,099 B2 * | 7/2008 | Stokes | 362/103 |
| D579,133 S | 10/2008 | Shiu | |
| D596,325 S | 7/2009 | Barbour | |
| D605,319 S | 12/2009 | Devaney et al. | |
| D608,485 S | 1/2010 | Liao et al. | |
| D615,678 S | 5/2010 | DeBrunner | |
| D615,680 S | 5/2010 | Kim | |
| 7,815,334 B2 | 10/2010 | Sherman | |
| D658,323 S | 4/2012 | Freschl | |
| 8,157,401 B2 | 4/2012 | Lau | |
| D676,991 S | 2/2013 | Araujo et al. | |
| D690,855 S | 10/2013 | Araujo et al. | |
| 2001/0048596 A1 * | 12/2001 | Kerr | 362/110 |
| 2003/0002297 A1 * | 1/2003 | Nemtsev | 362/571 |
| 2005/0018544 A1 | 1/2005 | Galli | |
| 2005/0254229 A1 * | 11/2005 | Hamade et al. | 362/103 |
| 2006/0104046 A1 * | 5/2006 | Guzman | 362/103 |
| 2007/0058362 A1 * | 3/2007 | Winfrey | 362/103 |
| 2007/0147025 A1 | 6/2007 | Shirey | |
| 2007/0279894 A1 * | 12/2007 | Esses | 362/103 |
| 2008/0062676 A1 * | 3/2008 | Masuda | 362/103 |
| 2008/0218996 A1 * | 9/2008 | Galloway et al. | 362/103 |
| 2008/0250672 A1 * | 10/2008 | Forbes | 36/137 |
| 2009/0108039 A1 * | 4/2009 | Sherman | 224/577 |
| 2009/0167542 A1 * | 7/2009 | Culbert et al. | 340/635 |
| 2009/0284216 A1 * | 11/2009 | Bessa et al. | 320/101 |

OTHER PUBLICATIONS

U.S. Appl. No. 29/436,349, filed Nov. 5, 2012, inventors: Port et al., 10 pages.
U.S. Appl. No. 29/436,351, filed Nov. 5, 2012, inventors: Matthews et al., 10 pages.

* cited by examiner

WEARABLE LIGHTING DEVICE

BACKGROUND

1. Field of the Invention

The disclosure generally relates to lighting devices and more particularly to wearable lighting devices.

2. Related Art

Various types of lighting devices may be used to illuminate areas of interest. For example, portable lighting devices are often used by law enforcement, military personnel, emergency/medical personnel, divers, hikers, search/rescue teams, and other users.

However, many existing portable lighting devices are cumbersome to use, especially in urgent circumstances. For example, flashlights require a user to dedicate one hand to holding and pointing the flashlight in order to provide illumination. As a result, flashlights encumber the user and are especially difficult to handle when the user desires to simultaneously perform other activities such as operating a weapon or other equipment, providing hand or arm signals, taking offensive or defensive actions, or other activities. Indeed, certain flashlights may require the user to hold the flashlight in one hand and operate a switch of the flashlight with the other hand. In such cases, both of the user's hands may be at least temporarily occupied by the flashlight and are thus not available to perform other activities.

Headlamps are another type of portable lighting device. Although headlamps need not be held in the user's hand, they may still be cumbersome to wear and may require time to locate and install on the user's head. Such implementations may be inconvenient and impractical when illumination is needed quickly and unexpectedly. Moreover, headlamps may still require the user to use one or more hands to operate a switch during use.

Accordingly, there is a need for an improved lighting device that overcomes one or more of the deficiencies discussed above.

SUMMARY

In accordance with various embodiments described herein, a wearable device may be implemented with a light source to provide illumination to an area of interest. In one embodiment, the light source may be selectively operated by, for example, switches, physical displacement (e.g., movement) of the device, or other approaches. In another embodiment, the device may be implemented as a wristwatch to display time, date, or related information to a user.

In another embodiment, the device may be implemented with appropriate processing or communication components to perform other tasks. Such tasks may include but are not limited to: providing and storing (e.g., recording) position information (e.g., using the global positioning system (GPS) or other systems); providing and storing orientation information (e.g., compass headings or device displacement); performing data communication and storing of data (e.g., using voice or other sounds, video, or other types of data); displaying and storing other information (e.g., battery level and runtime, user movements which may be used to operate the light source, signal receipt and processing, or other information); downloading or uploading (e.g., by Universal Serial Bus (USB) or otherwise), storing, and displaying user selected operating conditions or menus; or other tasks or combinations of tasks.

In another embodiment, a wearable device includes a light source adapted to emit light from the device to illuminate an area of interest external to the device; a display adapted to provide information to a user of the device; a motion detector adapted to detect a predetermined movement of a user wearing the device, wherein the motion detector generates a motion detection signal upon detection of the movement by the user; and a circuit adapted to selectively operate the light source in response to the motion detection signal and further adapted to provide the information to the display.

In another embodiment, a wearable device includes a light source adapted to emit light from the device to illuminate an area of interest external to the device; a motion detector adapted to detect a predetermined movement of a user wearing the device, wherein the motion detector generates a motion detection signal upon detection of the movement by the user; and a circuit adapted to selectively operate the light source in response to the motion detection signal.

In another embodiment, a wearable device includes a light source adapted to emit light from the device to illuminate an area of interest external to the device; and a lens adapted to project the light substantially in a direction that is inclined relative to an arm of the user when the device is worn on the arm of the user, wherein the direction of the light is inclined at an angle of approximately 35 degrees relative to the arm of the user.

In other embodiments, various methods of using, operating, or manufacturing such devices are provided.

The scope of the invention is defined by the claims, which are incorporated into this section by reference. A more complete understanding of embodiments of the disclosure will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE FIGURES

Embodiments of the disclosure and their advantages are best understood by referring to the detailed description that follows. It should be appreciated that like reference numerals are used to identify like elements illustrated in one or more of the figures.

DETAILED DESCRIPTION

Figure 1A:
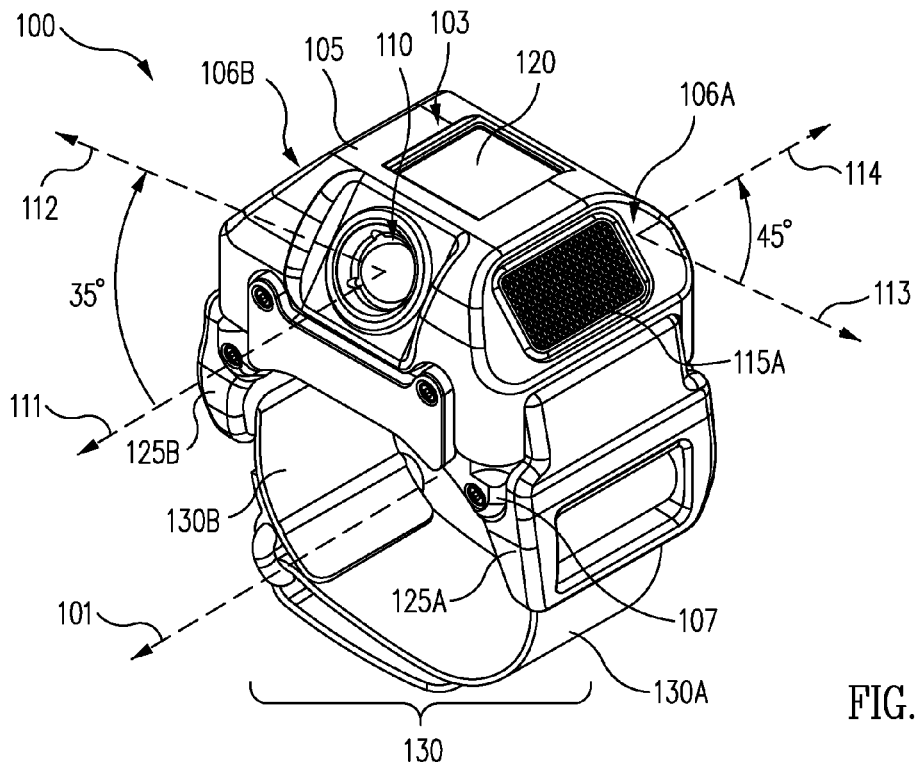
FIGS. 1A-H illustrate external views of a wearable device in accordance with various embodiments of the disclosure.
Figure 1B:
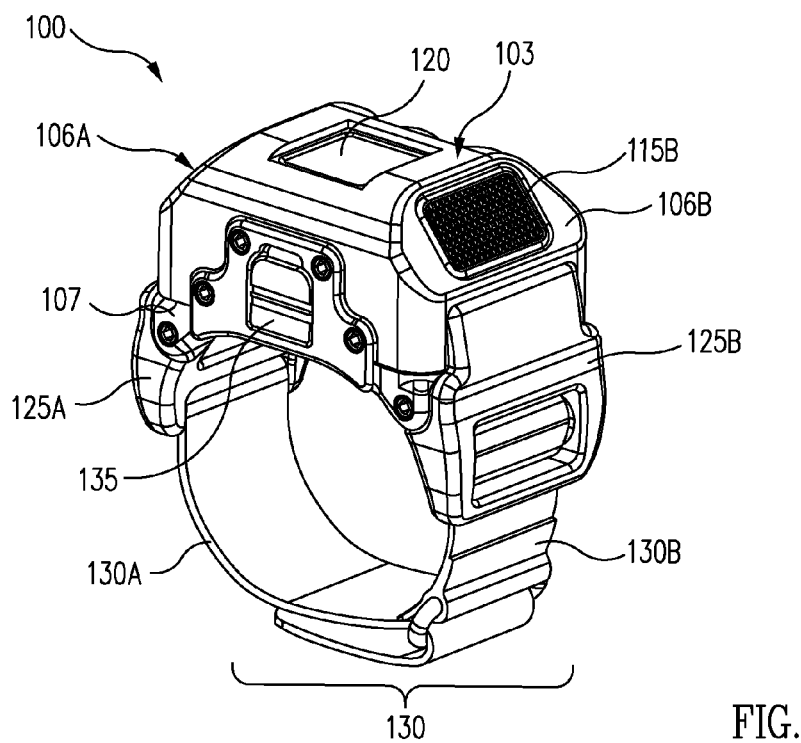
Figure 1C:
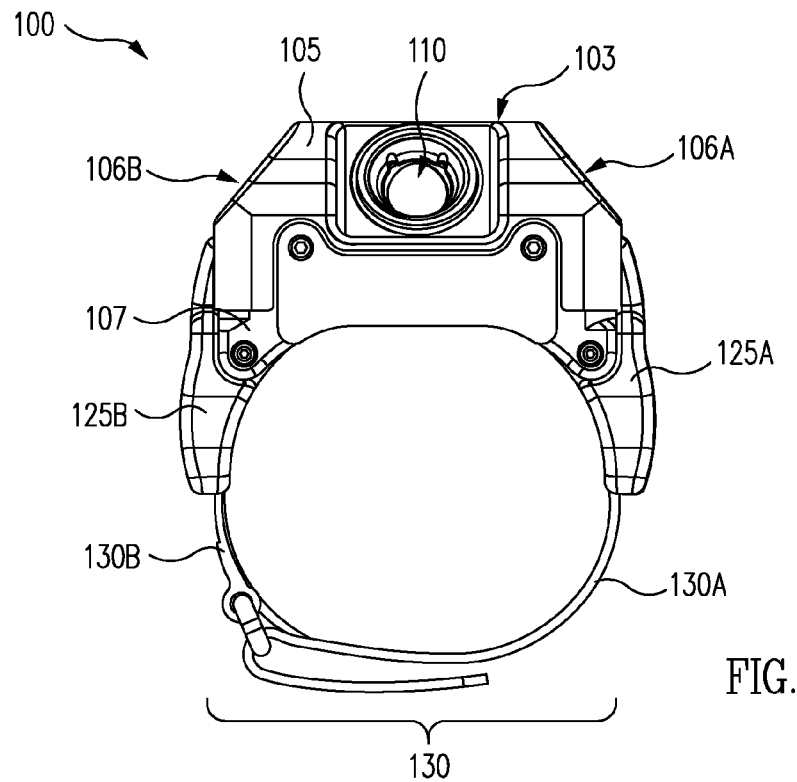
Figure 1D:
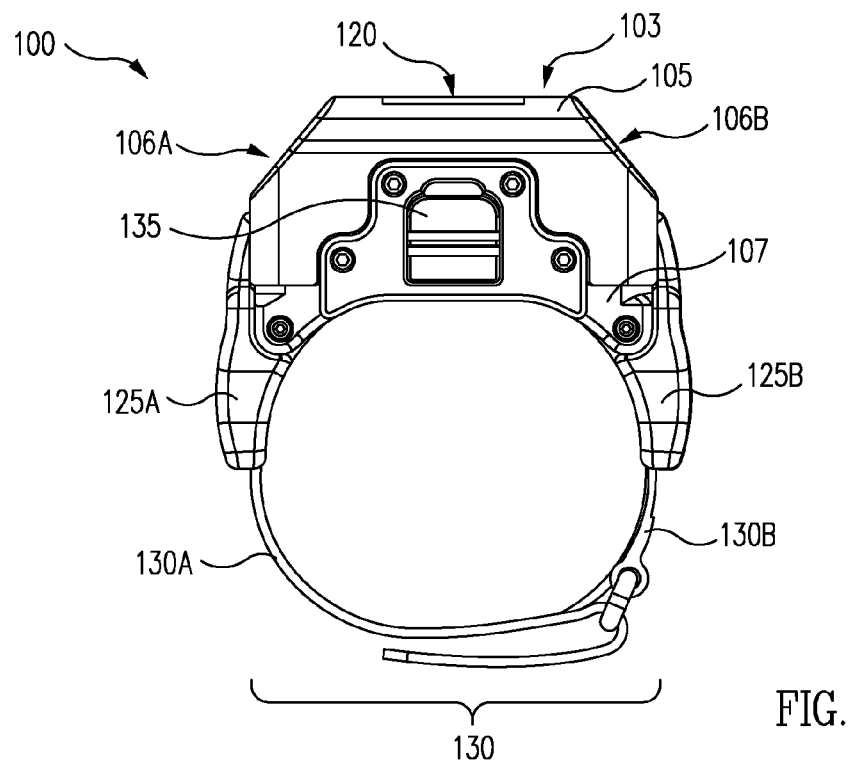
Figure 1E:
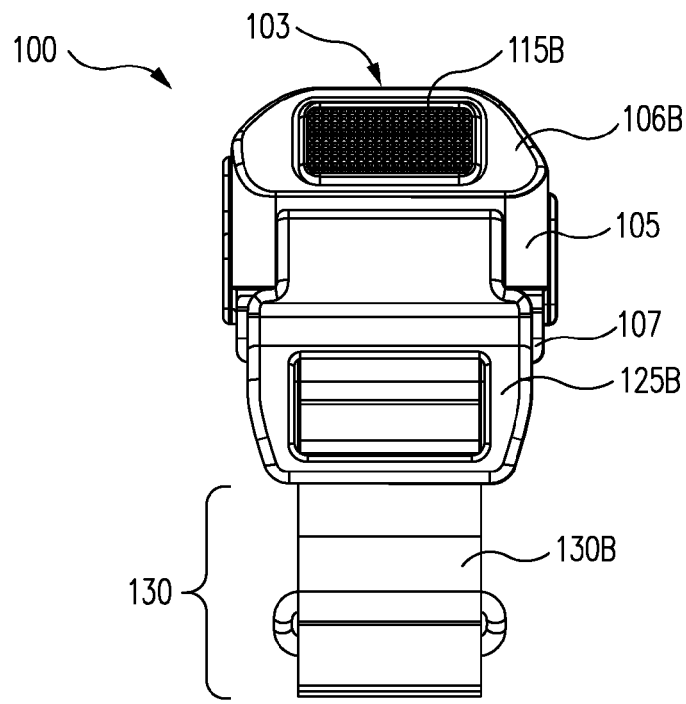
Figure 1F:
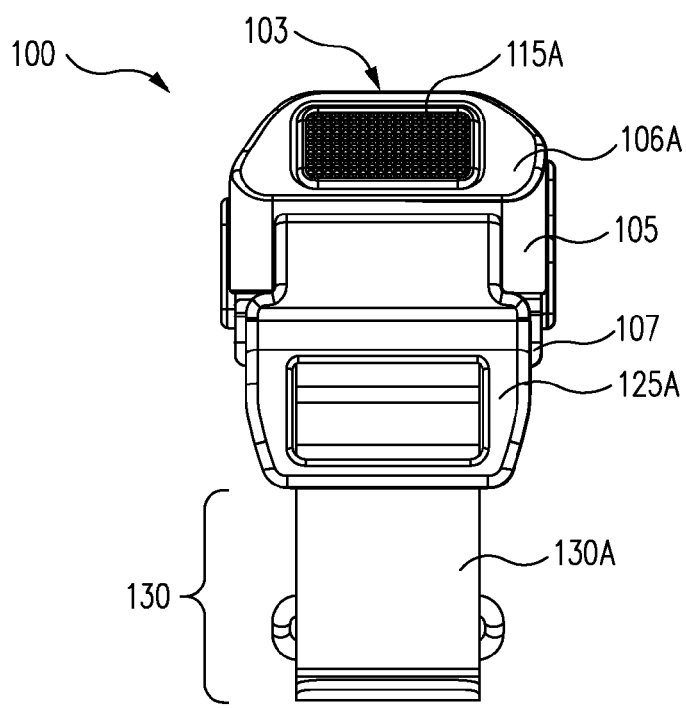
Figure 1G:
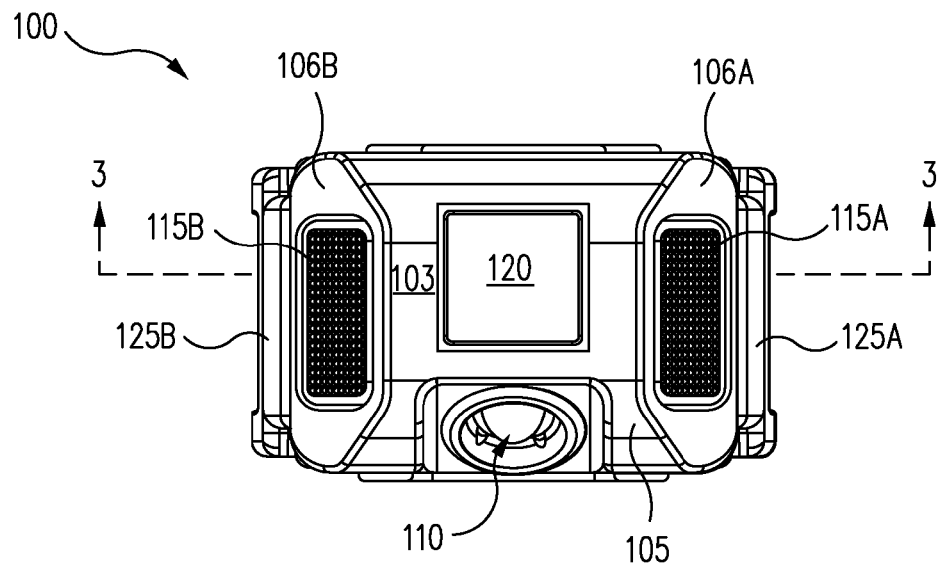
Figure 1H:
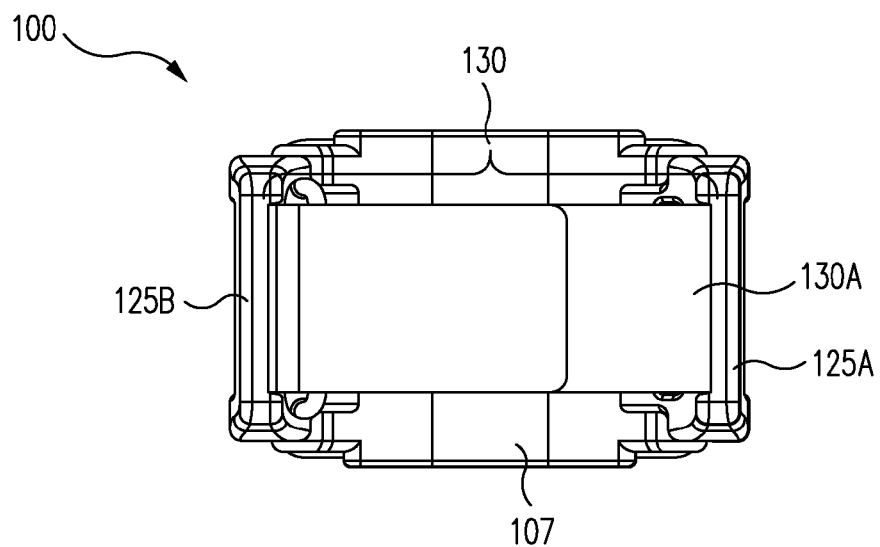

FIGS. 1A-H illustrate external views of a wearable device 100 in accordance with various embodiments of the disclosure. In one embodiment, device 100 may be worn on an arm (e.g., the wrist, hand, forearm, or upper arm) of the user while the hand of the user extends in the direction of an arrow 101. The user may operate device 100 by performing one or more actions such as, for example, pressing one or more switches, moving device 100 according to a particular pattern (e.g., physically translating device 100 in one or more directions), or other actions.

Device 100 includes an optical assembly 110 mounted in a housing including a body 105 and a base 107. In one embodiment, optical assembly 110 may be oriented (e.g., inclined) at an angle of approximately 35 degrees (see arrows 111 and 112) relative to the user's arm (see arrow 101 which is parallel to arrow 111). In this configuration, optical assembly 110 is also oriented at an angle of approximately 55 degrees relative to a top surface 103 of body 105. When the user's arm is extended in the direction of arrow 101, optical assembly 110 may project light substantially in the direction of arrow 112. In one embodiment, optical assembly 110 may include one or more light sources and a total internal reflection (TIR) lens to project a light beam having a spread of approximately 60 degrees. In one embodiment, optical assembly 110 may include optics for projecting diffuse light beams useful for navigation.

Figure 2:
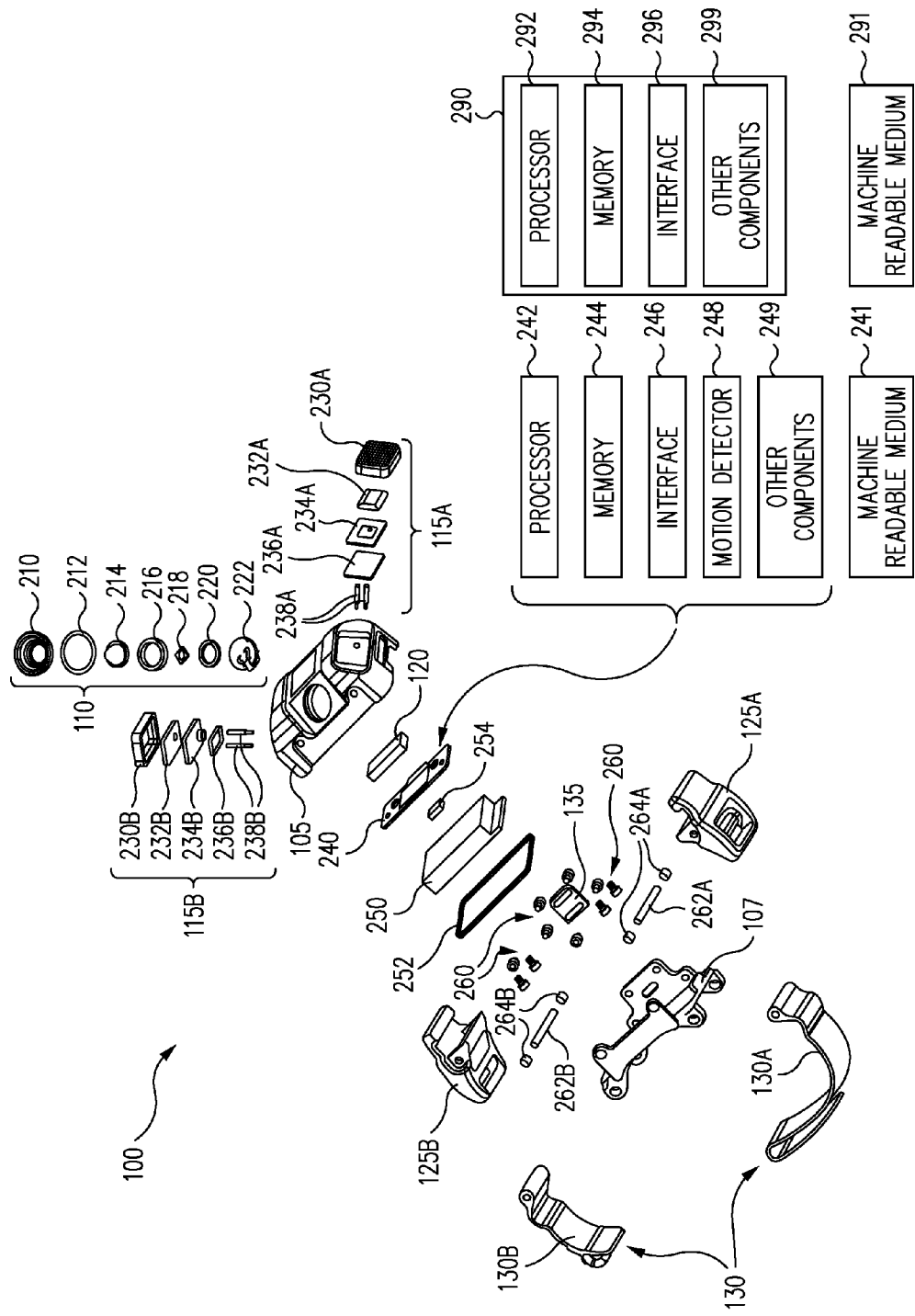
FIG. 2 illustrates an exploded view of the device of FIGS. 1A-H in accordance with an embodiment of the disclosure.

In one embodiment, body 105 and base 107 may provide a heat sink for components (further described herein) provided within device 100. For example, body 105 and base 107 may be made of magnesium, lightweight aluminum, or other materials as desired to operate as a heat sink. In this regard, a seal 252 as shown in FIG. 2 (e.g., implemented as a thermally conductive gasket, an o-ring, or other appropriate component) may be provided between body 105 and base 107 and may dissipate (e.g., conduct) heat between body 105 and base 107. For example, heat may be dissipated: from components within device 100 to body 105, base 107, and seal 252; from body 105 to base 107 through seal 252; from base 107 to the arm (e.g., the wrist, hand, forearm, or upper arm) of the user; or any other appropriate manner.

Figure 10:
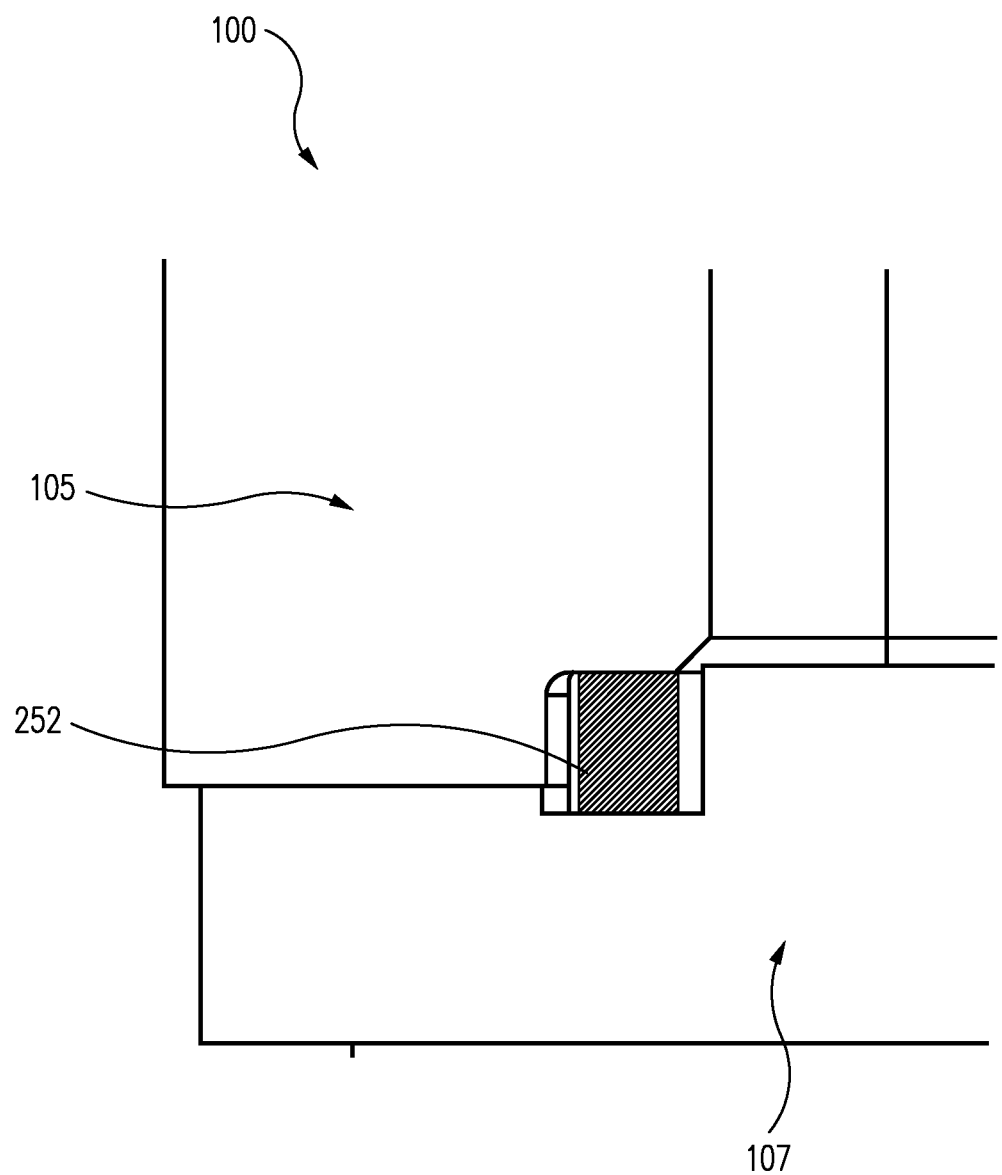
FIG. 10 illustrates a portion of the device of FIGS. 1A-H in accordance with an embodiment of the disclosure.

For example, FIG. 10 illustrates a portion of device 100 in accordance with an embodiment of the disclosure. In particular, FIG. 10 illustrates relative positions of body 105, base 107, and seal 252 when device 100 is assembled. In one embodiment, seal 252 permits body 105 to be coupled to base 107 in a thermally conductive manner, and also serves as a water proof seal. Advantageously, this embodiment permits the user's arm (e.g., the wrist, hand, forearm, or upper arm) to act as a heat sink to draw away heat from body 105, base 107, and seal 252, and dissipate such heat in or on the human body.

Body 105 includes sides 106A-B. In one embodiment, sides 106A-B may be oriented (e.g., inclined) at angles of approximately 45 degrees (see arrows 113 and 114) relative to a plane provided by arrows 111 and 113. In this configuration, sides 106A-B are also oriented at angles of approximately 45 degrees relative to top surface 103 of body 105.

Switches 115A-B are mounted on sides 106A-B. In one embodiment, switches 115A-B may be oriented at angles of approximately 45 degrees in the same fashion as sides 106A-B. Such positioning may facilitate convenient operation of switches.

Switches 115A-B may be used to selectively operate optical assembly 110 in response to user manipulation. In one embodiment, switches 115A-B may perform the same operations. As a result, the user may operate device 110 using one or both of switches 115A-B as desired for convenient, ambidextrous, and rapid operation of device 110. In one embodiment, pressing either of switches 115A-B in succession may switch one or more light sources of optical assembly 110 between off, low illumination, and high illumination settings. A low illumination setting may be particularly useful for law enforcement when writing tickets or performing other operations.

In another embodiment, switches 115A-B may each perform a different operation in response to user manipulation. In yet other embodiments, switches 115A-B may be implemented to perform other operations as may be desired for particular implementations.

A display 120 may provide information to the user of device 100. In one embodiment, device 100 may operate as a wristwatch. In this case, display 120 may present time, date, or other related information. In other embodiments, other information may be displayed. In another embodiment, display 120 may be a touch screen configured to receive tactile inputs from the user to display desired information or perform other tasks. In various embodiments, display 120 may be implemented using any desired type of display such as a liquid crystal display (LCD), one or more light emitting diodes (LEDs), or other types.

Body 105 is mounted on base 107. In various embodiments, base 107 may be made of the same material as body 105, or different material.

Stabilizers 125A-B are attached to body 105, base 107, and a strap 130. In this regard, stabilizers 125A-B provide attachment points for portions 130A-B of strap 130. In various embodiments, stabilizers 125A-B may be made of urethane or other materials. In one embodiment, strap 130 may be used to attach device 100 to an arm of the user. In other embodiments, strap 130 may be used to attach device 100 to other locations or positions (e.g., attached to a person, attached to an object, or attached elsewhere). In various embodiments, strap 130 may be made of military specification ballistic nylon or other materials.

An interface port 135 may be used to selectively connect device 100 to other devices. For example, in one embodiment, interface port 135 may include a Universal Serial Bus (USB) port (e.g., a micro USB connector 254 shown in FIG. 2 or other appropriate interface) mounted behind a door (shown in FIGS. 1B and 1D) which may be selectively opened or closed by the user. In this regard, interface port 135 may be used to charge device 100 or pass data between device 100 and one or more other connected devices. In another embodiment, interface port 135 may be implemented as a power charging port configured to receive a connector (e.g., a barrel plug connector or other appropriate connector) from a power supply.

Figure 3:
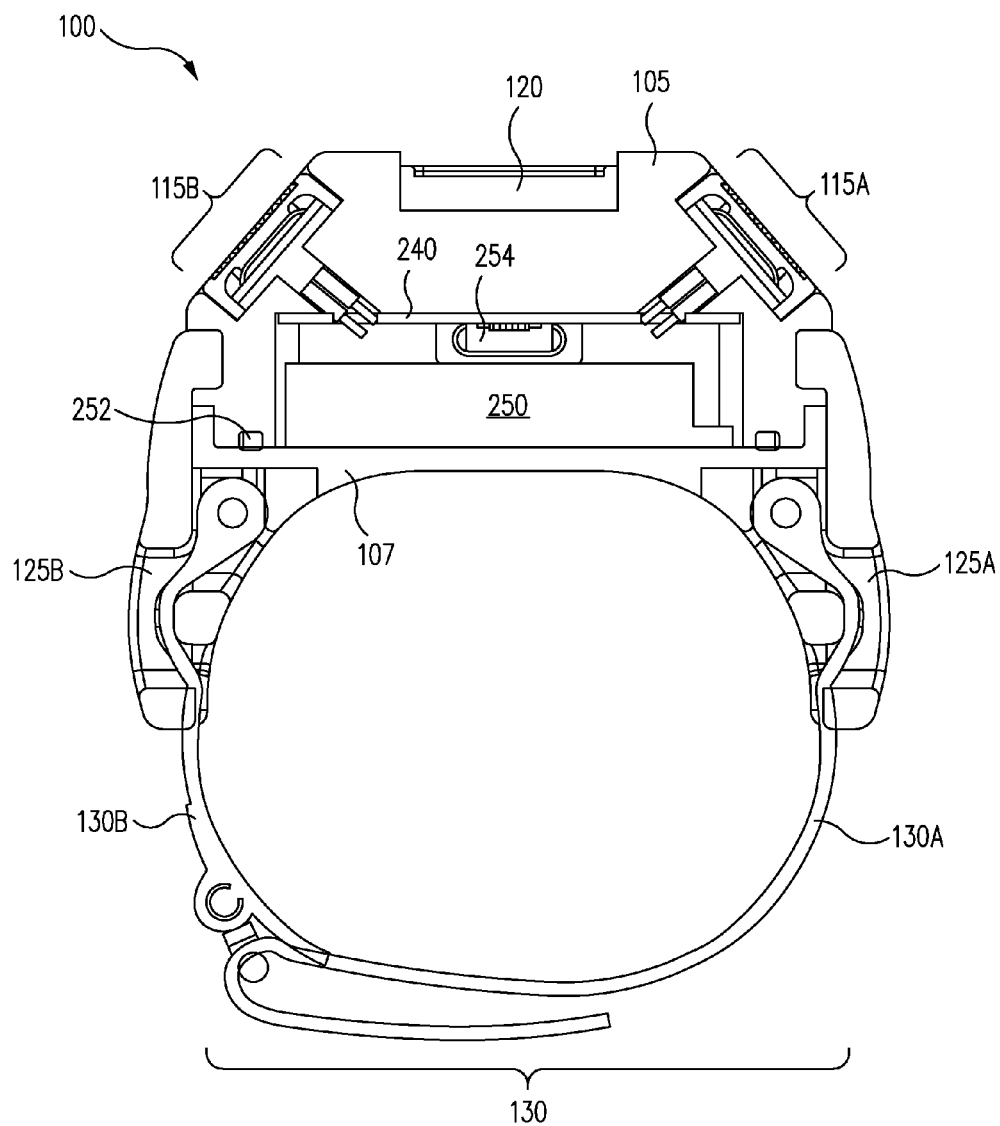
FIG. 3 illustrates a cross-sectional view of the device of FIGS. 1A-H taken at line 3-3 of FIG. 1G in accordance with an embodiment of the disclosure.

FIG. 2 illustrates an exploded view of device 100 in accordance with an embodiment of the disclosure. FIG. 3 illustrates a cross-sectional view of device 100 taken at line 3-3 of FIG. 1G in accordance with an embodiment of the disclosure. FIGS. 2 and 3 illustrate various components of device 100 shown in FIGS. 1A-H, as well as additional components of device 100.

Optical assembly 110 includes a retainer 210, an o-ring 212, a lens 214 (e.g., a TIR lens or other type of lens), a spacer 216, a light source 218 (e.g., one or more light emitting diodes (LEDs), filament lamps, arc lamps, or any other light sources to emit or project light), a seal 220, and a printed circuit board (PCB) 222 (e.g., to provide electrical connections between light source 218 and other components of device 100 as appropriate).

Switches 115A-B include caps 230A-B, contacts 232A-B (e.g., which may be selectively opened or closed in response to the user's pushing on caps 230A-B), PCBs 234A-B (e.g., to provide electrical connections between contacts 232A-B and other components of device 100 as appropriate), bottom receivers 236A-B, and wires 238A-B (e.g., to provide electrical connections between PCBs 234A-B and other components of device 100 as appropriate).

Device 100 also includes a PCB 240 which may be implemented with various components to support the operation of device 100. In one embodiment, device 100 includes a processor 242, a memory 244, an interface block 246, a motion detector 248, and various other components 249 as may be desired for particular implementations.

Processor 242 may execute various instructions stored in memory 244 or stored on a machine readable medium 241 (e.g., a non-transitory storage medium on which instructions such as software, microcode, or other instructions may be stored) to perform various operations as may be desired in various implementations. In various embodiments, processor 242 may be implemented by one or more logic circuits, programmable logic devices (PLDs), general purpose processors, application-specific integrated circuits (ASICs), or other appropriate circuitry.

In one embodiment, processor 242 may operate light source 218 (e.g., switch on, switch off, or adjust the intensity (e.g., brightness) of light source 218) in response to the user's operation of one or both of switches 115A-B.

In another embodiment, processor 242 may selectively operate light source 218 or perform other operations in response to one or more movements (e.g., predetermined programmed movements) of device 100 as detected by motion detector 248 (e.g., one or more accelerometers, inertial measurement units (IMUs), gyroscopes, microelectromechanical systems (MEMS) devices, or any other appropriate motion detector). In this regard, motion detector 248 may provide a motion detection signal (e.g., one or more signals) to processor 242. Processor 242 may operate device 100 in a tactical mode such that motion detection signals provided by motion detector 248 in response to various movements of the user wearing device 100 may result in processor 242 operating light source 218 or performing other operations without requiring the user to actuate a button or other control of device 100.

In another embodiment, processor 242 may operate to provide wristwatch features to display time, date, or related information on display 120 (e.g., PCB 240 may include appropriate circuitry to interface processor 242 with display 120).

In another embodiment, processor 242 may operate to provide and store position information using GPS or other systems (e.g., one or more antennas may be provided by other components 249).

In another embodiment, processor 242 may operate to provide and store orientation information such as compass headings or device displacement (e.g., as detected by motion detector 248 or other components 249 as appropriate). For example, processor 242 may store (e.g., in memory 244) data regarding movements of device 100 in response to signals received from motion detector 248. Such data may be used to determine the movements of the user's arm for training, archiving, or reporting purposes, and may be uploaded or downloaded in accordance with various techniques discussed herein.

In another embodiment, processor 242 may operate to perform data communication and store data using various types of data such as voice or other sounds, video, or other types of data (e.g., through interface port 135 (e.g., supporting any desired wired or wireless communication technique such as, for example, TCP/IP, Bluetooth, WiFi, or other communication techniques), or one or more antennas (e.g., supporting any desired wireless communication technique such as, for example, Bluetooth, WiFi, or other communication techniques), speakers, or microphones provided by other components 249).

In another embodiment, processor 242 may operate to display and store other information (e.g., such as battery level and runtime, user movements which may be used to operate light source 218, signal receipt and processing, or other information).

In another embodiment, processor 242 may operate to interface with other devices through interface port 135 or one or more antennas provided by other components 249 (e.g., interface block 246 may be used to connect processor 242 to micro USB connector 254, one or more antennas, or other appropriate connections). Such interfacing may permit device 100 to download, upload, store, and display any desired data or information such as configuration information of device 100 (e.g., user selected operating conditions, menus, or other information), data that identifies movements of device 100, or other data or information.

Although various particular examples of the operation of processor 242 and other components have been described, any desired features may be implemented by executing appropriate instructions by processor 242. Where desired, processor 242 and other components may be replaced or supplemented with other circuits or components to provide the various operations discussed herein.

Device 100 also includes a battery 250 (e.g., a Sanyo lithium-ion battery No. UF752836F in one embodiment) which may be used to power the various components of device 100. Battery 250 may be recharged through interface port 135 or a power charging port as desired. Device 100 also includes seal 252 which may provided between body 105 and base 107. Device 100 also includes screws 260 which may be used to assemble device 100. Device 100 also includes pins 262A-B and springs 264A-B which may be used to attach portions 130A-B of strap 130 to base 107. In various embodiments, the components of device 100 may be assembled in any desired fashion using, for example, screws, pressure, adhesive, or other manufacturing techniques.

Other embodiments are also contemplated. For example, in one embodiment, one or more components of device 100 (e.g., components installed within body 105 or base 107, or other components) may be selectively removed and replaced by the user. For example, it is contemplated that such components may be implemented in a drop-in module which may be selectively installed and removed from device 100. In this regard, different modules may be selectively installed in device 100 to provide different operations as may be desired in particular implementations.

In one embodiment, one or more components of PCB 240 may be replaced by dedicated hardware configured to implement a wristwatch (e.g., as a drop-in module or otherwise).

One or more additional machine readable mediums 291 may be provided to store instructions to be executed by an external device 290 (e.g., a computer or other device) including a processor 292, a memory 294, an interface block 296, and other components 299 (e.g., which may be implemented in the same or a different fashion from similar components of device 100) to permit the user to configure and customize settings and display 120 of device 100. Such information or other data may be downloaded to device 100 from device 290, or uploaded from device 100 to device 290, through interface port 135.

Figure 4:
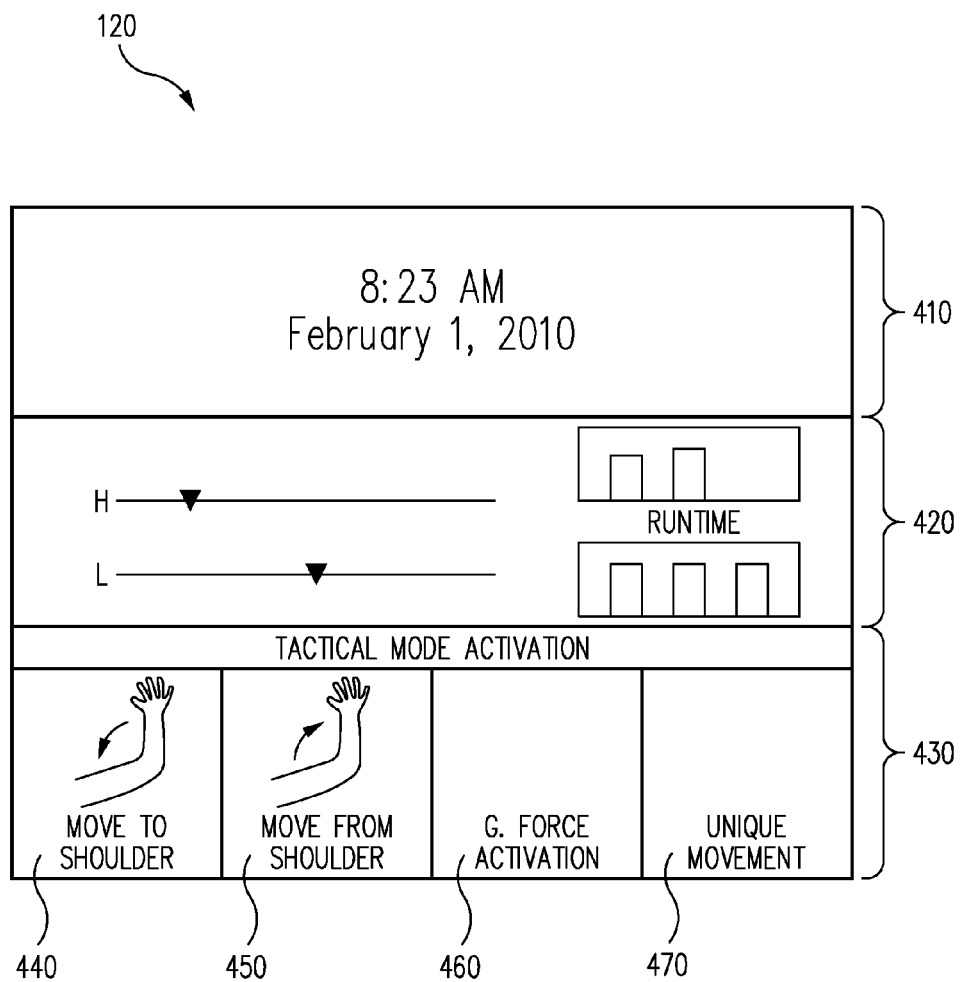
FIG. 4 illustrates a display of the device of FIGS. 1A-H in accordance with an embodiment of the disclosure.

FIG. 4 illustrates display 120 of device 100 in accordance with an embodiment of the disclosure. In FIG. 4, display 120 provides examples of various information which may be shown on display 120. In an area 410, display 120 provides current time and date information. In an area 420, display 120 provides battery status information and light intensity information (e.g., the current illumination setting of light source 218).

In an area 430, display 120 provides tactical mode activation information. As discussed, processor 242 may operate device 100 in a tactical mode such that various movements of device 100 may result in processor 242 operating light source 218 or performing other operations without requiring the user to actuate a button or other control of device 100. Such features may permit hands free operation of device 100 which may be particularly useful in law enforcement, military, and emergency situations to save time (e.g., instead of requiring the user to retrieve a conventional flashlight from a holster or search for a switch to operate a light source) or where neither of the user's hands is free to access switches 115A-B.

Area 430 identifies different types of movements that may be used to cause processor 242 to operate light source 218 or perform other operations. In various embodiments, different operations or the same operation may be performed in response to different movements.

Such movements may include, for example: moving device 100 from a position above the user's head and down toward the user's shoulder in a "move to shoulder" movement 440; moving device 100 from the user's shoulder to a position above the user's head in a "move from shoulder" movement 450; moving device 100 with a minimum, maximum, or range of acceleration (e.g., provided by gravity, user motion, or otherwise) in an "acceleration" or "G. Force" activation movement 460; and moving device 100 in a "unique" movement 470 (e.g., moving device 100 to a drawn gun position, hitting the user's chest, or another movement).

As discussed, optical assembly 110 may be oriented at an angle of approximately 35 degrees relative to the user's arm. Advantageously, such an orientation permits optical assembly 110 to illuminate areas of interest that normally would not be illuminated by conventional weapon mounted lights.

Figure 5:
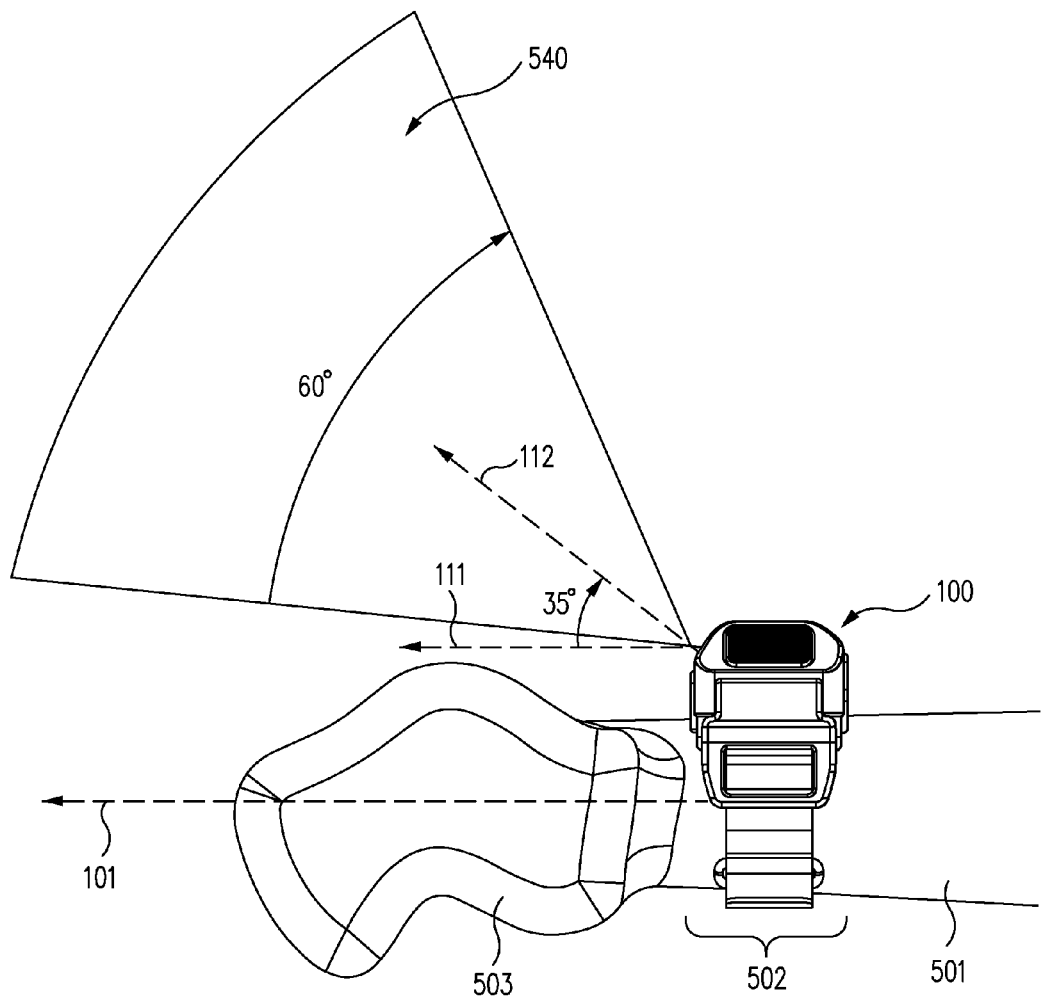
FIGS. 5-7 illustrate the device of FIGS. 1A-H as worn by a user in accordance with an various embodiments of the disclosure.
Figure 6:
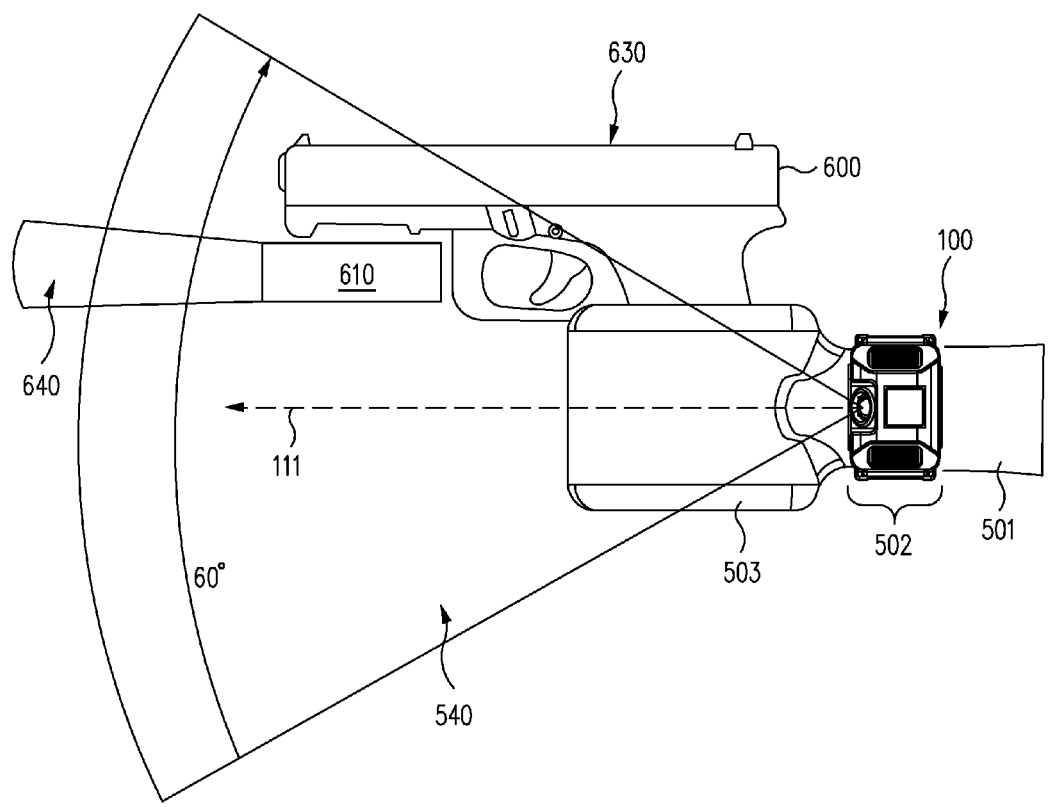
Figure 7:
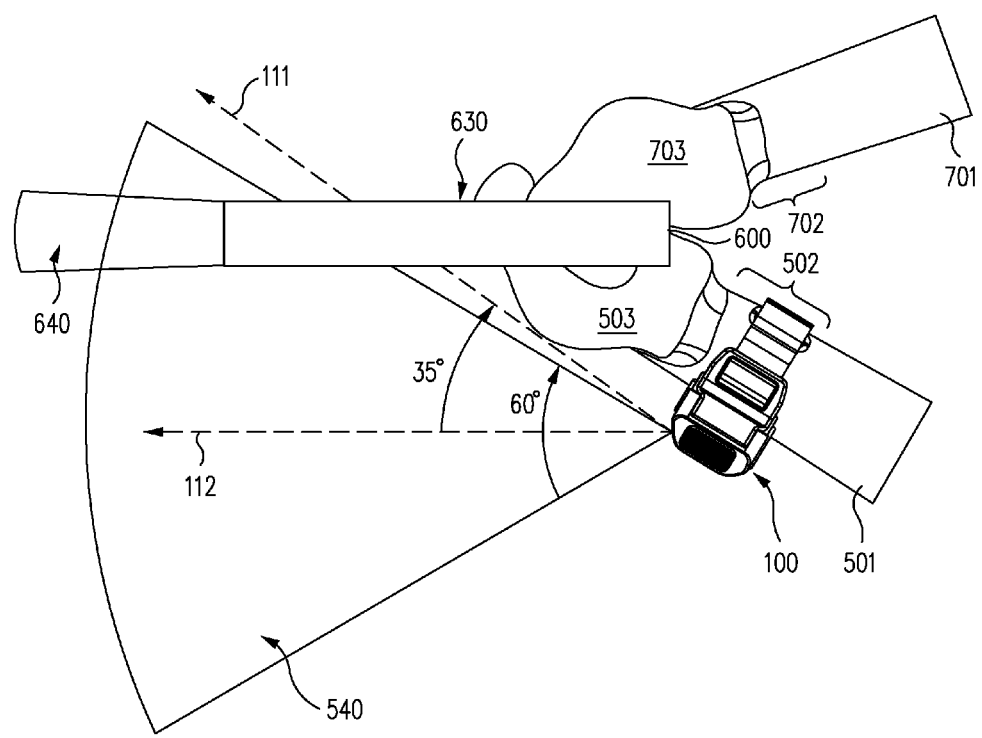

For example, FIGS. 5-7 illustrate the device of FIGS. 1A-H as worn by the user in accordance with an various embodiments of the disclosure. Specifically, FIG. 5 illustrates device 100 as worn on a wrist 502 of an arm 501 of the user. When arm 501 is extended parallel to arrow 101, device 100 projects a light beam 540 having a beam spread of approximately 60 degrees and inclined upward at an angle of approximately 35 degrees relative to arm 501, wrist 502, and a hand 503 of the user.

FIGS. 6 and 7 illustrate side and top views, respectively, of device 100 as worn on wrist 502 of arm 501 of the user while the user also holds a weapon 600. In another embodiment, device 100 may be worn on a wrist 702 of an arm 701 of the user. In FIGS. 6-7, weapon 600 is supported by both hands 503 and 703 of the user (e.g., in FIG. 6, arm 701, wrist 702, and hand 703 are obscured by arm 501, wrist 502, and hand 503). In other embodiments, weapon 600 may be supported by either of hands 503 or 703 individually.

As shown in FIG. 6, weapon 600 includes a conventional weapon mounted light 610. Weapon mounted light 610 projects a light beam 640 substantially parallel to a barrel 630 of weapon 600. Moreover, weapon mounted light 610 is mounted substantially underneath barrel 630 which is typical of such lights. As a result, weapon mounted light 610 projects very little, if any, light above barrel 630. Moreover, for long barrel weapons, weapon mounted light 610 may be mounted completely underneath the long barrel such that the long barrel blocks light from projecting upwardly past the long barrel.

When device 100 is positioned as shown in FIGS. 6-7, optical assembly 110 of device 100 may project light beam 540 upward and downward (see FIG. 6), and left and right (see FIG. 7), in a wide field of view of the user to illuminate areas of interest that would otherwise be in the blind spots of conventional weapon mounted lights. Such illumination is particularly advantageous in law enforcement situations.

Figure 8:
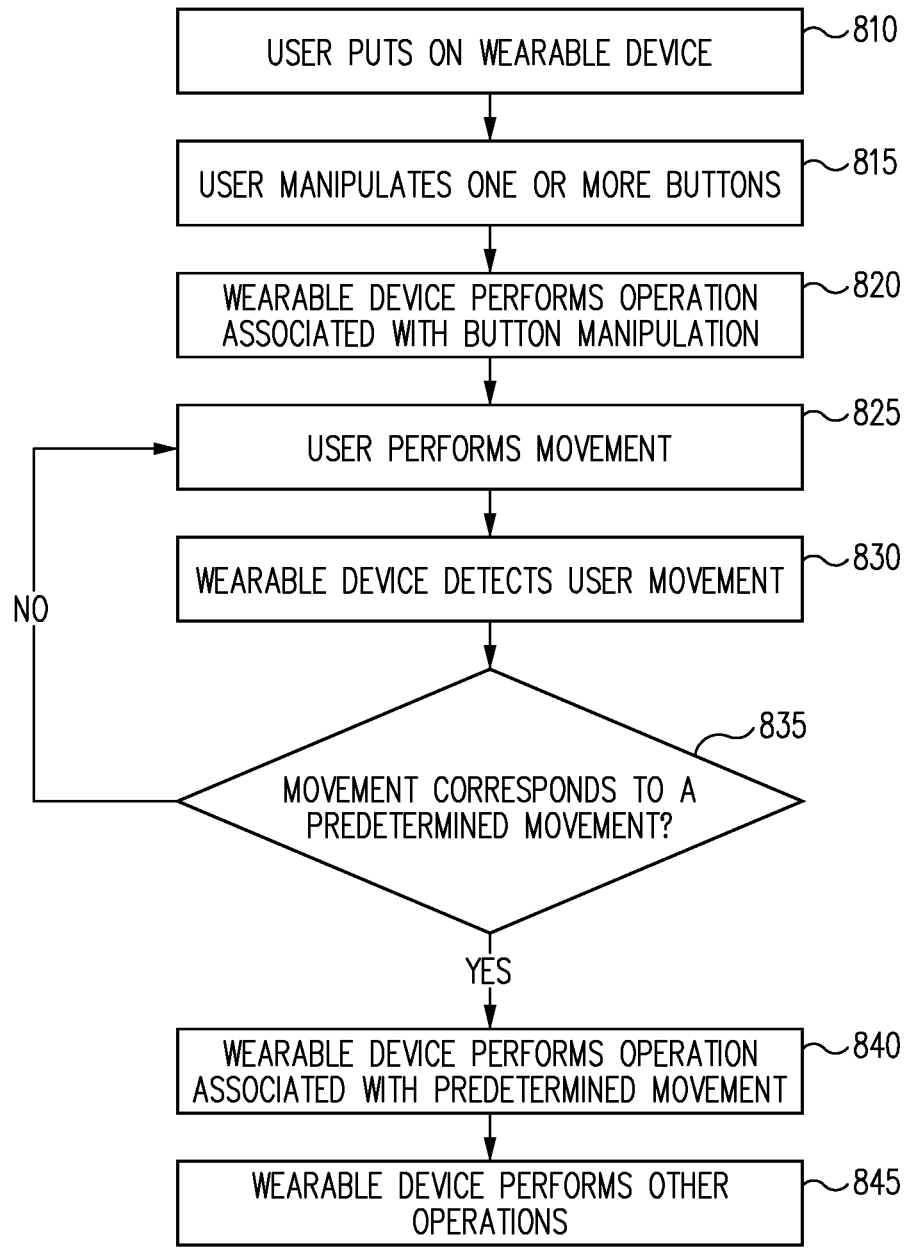
FIG. 8 illustrates a process of using of the device of FIGS. 1A-H in accordance with an embodiment of the disclosure.

As discussed, device 100 may be used in a variety of ways. For example, FIG. 8 illustrates a process of using device 100 in accordance with an embodiment of the disclosure. Although various operations are identified in FIG. 8, any desired operations may be performed and the operations may be reordered and repeated where appropriate as desired for particular applications.

In block 810, the user puts on device 100 by, for example, attaching device 100 to the user's arm. In block 815, the user manipulates one or more of buttons 115A-B or manipulates display 120 to initiate an operation to be performed by device 100. In block 820, device 100 performs an operation (e.g., by processor 242 executing instructions to perform any of the operations described herein) associated with the manipulation performed in block 815.

In block 825, the user performs a movement (e.g., any of the movements described herein) while wearing device 100. In block 830, device 100 detects the user movement performed in block 825 (e.g., by motion detector 248 detecting the movement and providing one or more motion detector signals to processor 242).

In block 835, device 100 determines (e.g., by processor 242 executing instructions) whether the detected movement corresponds to a predetermined movement (e.g., a predetermined movement identified by data stored in memory 244) that is associated with an operation (e.g., any of the operations described herein). In this regard, memory 244 may store data that identifies associations between one or more predetermined movements by a user and one or more operations to be performed by device 100.

If no association is found in block 835, then the process returns to block 825 where device 100 waits for another user movement to detect. If an association is found in block 835, then the process continues to block 840 where device 100 performs the operation (e.g., by processor 242 executing instructions to perform any of the operations described herein) associated with the detected user movement.

In block 845, device 100 performs other operations (e.g., any of the operations described herein) as may be desired in particular implementations.

Figure 9:
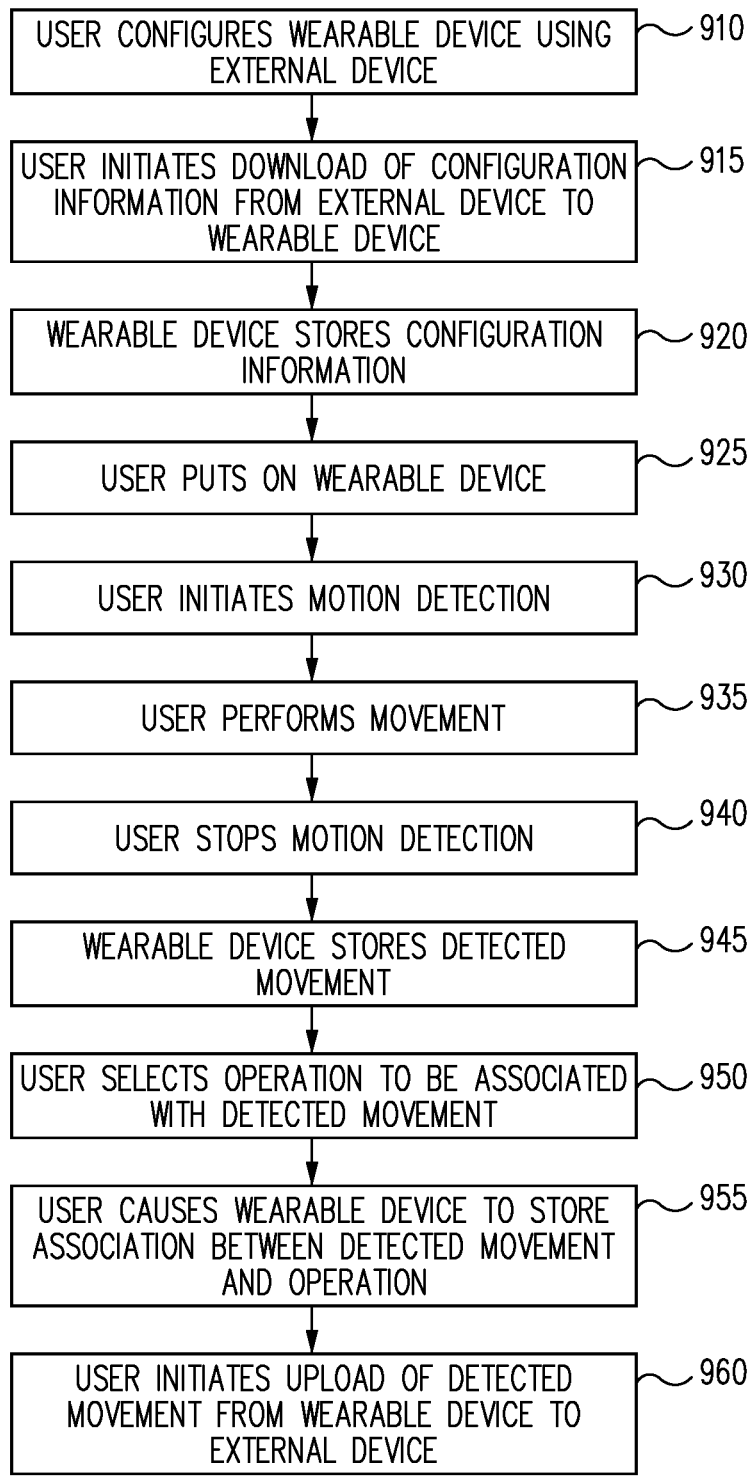
FIG. 9 illustrates a process of programming of the device of FIGS. 1A-H in accordance with an embodiment of the disclosure.

FIG. 9 illustrates a process of programming of device 100 in accordance with an embodiment of the disclosure. Although various operations are identified in FIG. 9, any desired operations may be performed and the operations may be reordered and repeated where appropriate as desired for particular applications.

In block 910, the user prepares configuration information for device 100 using external device 290 (e.g., by interacting with external device 290 through an appropriate software or hardware user interface to select or otherwise identify configurable features of device 100 such as operating conditions, menus, or other features).

In block 915, the user initiates a download of the configuration information from external device 290 to device 100. In this regard, the configuration information prepared in block 910 may be downloaded through interface port 245, an antenna provided by other components 249, or any other manner as appropriate. In block 920, device 100 stores the downloaded configuration information in memory 244.

In block 925, the user puts on device 100 (e.g., by strapping device 100 on to the user's arm or other appropriate location). In block 930, the user initiates motion detection (e.g., by manipulating one or more of buttons 115A-B or display 120 to cause processor 242 to prepare to receive or process one or more motion detection signals from motion detector 248). In block 935, the user performs a movement (e.g., any of the movements described herein) while wearing device 100. Also during block 935, motion detector 248 detects the user movement and provides one or more motion detection signals to processor 242. In block 940, the user stops motion detection (e.g., by manipulating one or more of buttons 115A-B or display 120 to cause processor 242 to stop receiving or processing one or more motion detection signals from motion detector 248). In block 945, device 100 stores data in memory 244 that identifies the detected user movement.

In block 950, the user selects an operation of device 100 to be associated with the detected movement (e.g., by manipulating one or more of buttons 115A-B or display 120 to cause processor 242 to select the operation). In block 955, the user causes device 100 to store data that identifies an association between the detected movement and the selected operation (e.g., by manipulating one or more of buttons 115A-B or display 120 to cause processor 242 to store such an association in memory 244). In block 960, the user initiates an upload of data device 100 to external device 290. Such data may include, for example, any of the data described herein.

In view of the disclosure, it will be appreciated that various embodiments of device 100 provide ways to conveniently and rapidly illuminate a wide field of view either with or without user manipulation of switches. Such features may be useful for a variety of different users and purposes including, for example, any gun carrying person (e.g., law enforcement, military, or others), firefighters, emergency and medical personnel, divers, hikers, search/rescue teams, and other users or purposes.

Where applicable, various embodiments provided by the disclosure can be implemented using hardware, software, or combinations of hardware and software. Also where applicable, the various hardware components and/or software components set forth herein can be combined into composite components comprising software, hardware, and/or both without departing from the spirit of the disclosure. Where applicable, the various hardware components and/or software components set forth herein can be separated into sub-components comprising software, hardware, or both without departing from the spirit of the disclosure. In addition, where applicable, it is contemplated that software components can be implemented as hardware components, and vice-versa.

Software in accordance with the disclosure, such as program code and/or data, can be stored on one or more machine readable mediums. It is also contemplated that software identified herein can be implemented using one or more general purpose or specific purpose computers and/or computer systems, networked and/or otherwise. Where applicable, the ordering of various steps described herein can be changed, combined into composite steps, and/or separated into sub-steps to provide features described herein.

Embodiments described above illustrate but do not limit the disclosure. It should also be understood that numerous modifications and variations are possible in accordance with the principles of the disclosure. Accordingly, the scope of the invention is defined only by the following claims.

What is claimed is:

1. A device wearable on a wrist of a user, the device comprising:
    a wrist strap;
    a housing connected to the wrist strap and substantially confined to the wrist while the wrist strap is worn by the user;
    a light source disposed substantially within the housing;
    a lens, separate from the light source, that receives light emitted by the light source and projects the light from an aperture in a front face of the housing to illuminate an area external to the device;
    wherein the lens is fixed relative to the front face of the housing, fixed relative to a bottom surface of the housing, and inclined to project the light with a maximum beam spread of approximately 60 degrees substantially centered about an axis at a fixed non-adjustable angle of approximately 35 degrees relative to the bottom surface of the housing, wherein the lens defines the maximum beam spread;
    wherein the fixed angle causes an edge of the maximum beam spread to be offset approximately 5 degrees relative to the bottom surface of the housing to prevent the projected light from overlapping onto a hand of the user associated with the wrist while the hand supports a firearm in a drawn position; and
    wherein the bottom surface of the housing is configured to be aligned on a top surface of the wrist while the user's palm is directed downwards and while the wrist strap is worn by the user.

2. The device of claim 1, wherein the lens is a total internal reflection (TIR) lens.

3. The device of claim 1, wherein the housing operates as a heat sink for the circuit to dissipate heat to the wrist.

4. The device of claim 3, wherein the housing comprises aluminum or magnesium.

5. The device of claim 1, further comprising:
    first and second buttons on first and second surfaces, respectively, of the housing, wherein the surfaces and the buttons are inclined relative to the bottom surface of the housing; and
    a circuit to selectively operate the light source in response to a manipulation of either of the buttons by the user.

6. The device of claim 5, wherein the surfaces and the buttons are inclined at angles of approximately 45 degrees.

7. The device of claim 1, further comprising:
    a processor; and
    a memmory.

8. The device of claim 7,
    wherein the processor executes instructions stored in the memory to selectively operate the light source.

9. The device of claim 7, wherein the processor executes instructions stored in the memory to download first data from an external device to the memory and upload second data from the memory to the external device.

10. The device of claim 9, wherein the first data comprises configuration information of the device.

11. The device of claim 9, further comprising an interface port, wherein the processor executes the instructions to download the first data and upload the second data through the interface port.

12. The device of claim 11, wherein the interface port is a Universal Serial Bus (USB) port.

13. The device of claim 9, further comprising an antenna, wherein the processor executes the instructions to download the first data and upload the second data through the antenna.

14. The device of claim 7, further comprising:
    an antenna; and
    a display, wherein the processor executes instructions stored in the memory to determine position information using one or more signals received by the antenna and provide the position information to the display.

15. The device of claim 7, further comprising:
a microphone; and
a speaker, wherein the processor executes instructions stored in the memory to store sounds received through the microphone and play back the sounds through the speaker.

16. The device of claim 1, further comprising a motion detector disposed substantially in the housing and that detects a particular predetermined movement of an arm the user while the wrist strap is worn by the user, wherein the motion detector generates a motion detection signal upon detection of the movement of the user.

17. The device of claim 16, further comprising:
a processor; and
a memory, wherein the processor executes instructions stored in the memory to upload to an external device data that identifies movements of the device detected by the motion detector.

18. A method of operating the device of claim 16, the method comprising:
attaching the device to the wrist; and
performing the particular predetermined movement.

19. The method of claim 18, further comprising causing the device to store data identifying the particular predetermined movement.

20. The method of claim 18, wherein the particular predetermined movement is a movement of the user to orient the firearm in the drawn position.

21. The device of claim 16, further comprising a circuit that selectively operates the light source in response to the motion detection signal.

22. The device of claim 1, further comprising:
a battery;
a display;
a port that receives power to charge the battery; and
a circuit that provides charge information for the battery to the display.

23. The device of claim 1, further comprising:
a display; and
a circuit that provides time information to the display.

24. A method of operating the device of claim 1, the method comprising causing the device to download first data from an external device and upload second data to the external device.

25. The method of claim 24, wherein the first and second data is downloaded and uploaded, respectively, through an interface port of the device.

26. The method of claim 24, wherein the first and second data is downloaded and uploaded, respectively, through an antenna of the device.

27. The method of claim 24, wherein the first data comprises configuration information of the device.

28. The method of claim 24, wherein the second data identifies movements of the device detected by a motion detector of the device.

29. A method of operating the device of claim 1, the method comprising:
causing the device to store sounds received through a microphone of the device; and
causing the device to play back the sounds though a speaker of the device.

30. A method of manufacturing the device of claim 1, the method comprising assembling the device.

31. A method of operating the device of claim 1, the method comprising performing an action to operate the light source.

32. A method comprising:
grasping a firearm with a first hand of a user;
supporting the firearm in a drawn position with a second hand of the user;
during the supporting, illuminating an external area toward which the firearm is directed using a lighting device attached to a wrist of the user associated with the second hand; and
wherein the lighting device comprises:
a wrist strap,
a housing connected to the wrist strap and substantially confined to the wrist,
a light source disposed substantially within the housing,
a lens, separate from the light source, that receives light emitted by the light source and projects the light from an aperture in a front face of the housing,
wherein the lens is fixed relative to the front face of the housing, fixed relative to a bottom surface of the housing, and inclined to project the light with a maximum beam spread of approximately 60 degrees substantially centered about an axis at a fixed non-adjustable angle of approximately 35 degrees relative to the bottom surface of the housing and substantially parallel to a barrel of the firearm, wherein the lens defines the maximum beam spread,
wherein the beam spread is a maximum beam spread of approximately 60 degrees, wherein the fixed angle causes an edge of the maximum beam spread to be offset approximately 5 degrees relative to the bottom surface of the housing to prevent the projected light from overlapping onto the second hand of the user while supporting the firearm in the drawn position, and
wherein the bottom surface of the housing is aligned on a top surface of the wrist disposed away from the firearm.

* * * * *

UNITED STATES PATENT AND TRADEMARK OFFICE
CERTIFICATE OF CORRECTION

| | | |
|---|---|---|
| PATENT NO. | : 9,155,168 B2 | Page 1 of 1 |
| APPLICATION NO. | : 12/960376 | |
| DATED | : October 6, 2015 | |
| INVENTOR(S) | : Luis Araujo et al. | |

It is certified that error appears in the above-identified patent and that said Letters Patent is hereby corrected as shown below:

In the claims

In column 11, line 11, change "a particular predetermined movement of an arm the user" to --a particular predetermined movement of an arm of the user--.

Signed and Sealed this
Twenty-ninth Day of March, 2016

Michelle K. Lee
*Director of the United States Patent and Trademark Office*